(12) United States Patent
Sugiyama

(10) Patent No.: US 7,803,638 B2
(45) Date of Patent: Sep. 28, 2010

(54) FLUORESCENT LABEL

(75) Inventor: Masami Sugiyama, Tokyo (JP)

(73) Assignee: Fujirebio, Inc., Tokyo (JP)

( * ) Notice: Subject to any disclaimer, the term of this patent is extended or adjusted under 35 U.S.C. 154(b) by 442 days.

(21) Appl. No.: 11/379,617

(22) Filed: Apr. 21, 2006

(65) Prior Publication Data

US 2006/0240479 A1 Oct. 26, 2006

(30) Foreign Application Priority Data

Apr. 25, 2005 (JP) .......................... P 2005-126247

(51) Int. Cl.
G01N 33/533 (2006.01)
G01N 33/53 (2006.01)
G01N 21/76 (2006.01)

(52) U.S. Cl. .................. 436/546; 435/7.1; 436/106; 436/119; 436/172; 436/800

(58) Field of Classification Search ............ 436/528, 436/531, 532, 543, 56, 823
See application file for complete search history.

(56) References Cited

U.S. PATENT DOCUMENTS

| 4,434,150 A | 2/1984 | Azad et al. |
| 5,030,697 A * | 7/1991 | Hugl et al. ............... 525/326.9 |
| 5,189,029 A * | 2/1993 | Boyer et al. ................ 514/64 |
| 5,880,287 A * | 3/1999 | Dandliker et al. .......... 548/156 |
| 2002/0123068 A1 * | 9/2002 | Dwyer et al. ............... 435/7.1 |
| 2003/0040125 A1 * | 2/2003 | Bernatchez et al. ......... 436/518 |

FOREIGN PATENT DOCUMENTS

| EP | 0077671 | 4/1983 |
| EP | 0269451 | 6/1988 |

OTHER PUBLICATIONS

XP002437926, DataBase Compendex (Online) Engineering Information, Inc., New York, NY US (Nov. 28, 2004) (abstract).
Pendri et al, Poly(ethylene glycol) Florescent Linkers, Bioconjugate Chemistry, ACS, Washington, DC, US, vol. 6, No. 5, 1995, pp. 596-598 (3 pages).
European Search Search Report dated Jun. 27, 2007 issued in corresponding European Patent Application No. 06300384.2 (7 pages).

* cited by examiner

*Primary Examiner*—Shafiqul Haq
(74) *Attorney, Agent, or Firm*—Grossman, Tucker, Perreault & Pfleger, PLLC

(57) ABSTRACT

The present invention relates to a fluorescent label characterized by containing a hydrophilic polymer having an anionic group, a polyether derivative, and a phosphor, in which the phosphor is bound to the hydrophilic polymer via the polyether derivative, and also relates to a fluorescently labeled recognition substance labeled with the fluorescent label, and an immunoassay method using the recognition substance.

11 Claims, 4 Drawing Sheets

FLUORESCENT LABEL

BACKGROUND OF THE INVENTION

1. Field of the Invention

The present invention relates to a highly sensitive fluorescent label having a structure in which numerous phosphors are bound to a hydrophilic polymer via a polyether derivative, and also relates to a fluorescently labeled recognition substance labeled with the fluorescent label.

The present invention claims priority on Japanese Patent Application No. 2005-126247, filed on Apr. 25, 2005, the content of which is incorporated herein by reference.

2. Description of the Related Art

In the prior art, a method in which antigens or antibodies are labeled with radioisotopes, enzymes, phosphors, or the like and the intensity of signals emitted from these labels is measured is used so as to measure the concentration of the antigens or antibodies. However, the method using radioisotopes requires specific equipment and devices, and so has been scarcely used in recent years. Although a method exhibiting high sensitivity using luminous substrates has been widely used as the method using enzymes for labeling, the method requires expensive substrates and a relatively long time period for reacting the enzymes with the substrates, and so measurement cannot be performed over a short time.

In contrast, although the method using phosphors for labeling does not require specific equipment or devices or expensive substrates, it exhibits low sensitivity. In order to increase the sensitivity, it is required to introduce numerous phosphors into antibodies or the like. However, when numerous phosphors are directly bound to antibodies or the like, a quenching phenomenon occurs decreasing the fluorescence intensity, and the antibodies into which the phosphors are introduced gain increased hydrophobicity and are denatured. In order to solve this problem, a method in which a linker of a hydrophilic polymer is introduced into an antibody or the like and numerous phosphors are introduced into this linker has been proposed (see, for example, Japanese Unexamined Patent Application, First Publication No. S58-79162).

Although the above-mentioned method can prevent denaturation of the antibody or the like and decrease of the fluorescence intensity, a fluorescent label which can exhibit a higher fluorescence intensity is desired so as to improve the utility thereof.

SUMMARY OF THE INVENTION

The present invention relates to a fluorescent label including a hydrophilic polymer having an anionic group, a polyether derivative, and a phosphor, in which the phosphor is bound to the hydrophilic polymer via the polyether derivative.

The hydrophilic polymer may be one in which an acrylic acid derivative is polymerized.

The hydrophilic polymer may be one in which at least one selected from the group consisting of an acrylic acid, a methacrylic acid, a 2-aminoethyl methacrylate, a 3-sulfopropyl methacrylate, a 2-acrylamido-2-methylpropane sulfonate, a 2-ethyl methacrylic acid glucoside, and a N-acryloxysuccinimide is polymerized.

The hydrophilic polymer may have a molecular weight of 5 to 500 kDa.

The anionic group contained in the hydrophilic polymer may be at least one selected from the group consisting of a sulfonic acid group, a phosphoric acid group, and salts thereof.

The polyether derivative may be a polyethylene glycol derivative.

The polyether derivative may have a molecular weight of 0.1 to 50 kDa.

The number of phosphors may be within a range from 1 to 90.

The phosphor may be one selected from the group consisting of an indacene derivative, a fluorescein derivative, a rhodamine derivative, an indocarbocyanine derivative, and a furazan derivative.

Moreover, the present invention relates to a fluorescently labeled recognition substance labeled with the fluorescent label described above.

Also, the present invention relates to an immunoassay reagent containing the fluorescently labeled recognition substance described above.

Also, the present invention relates to an immunoassay method using the fluorescently labeled recognition substance described above.

DETAILED DESCRIPTION OF THE INVENTION

An object of the present invention is to provide a fluorescent label which can exhibit amplified fluorescence intensity without causing denaturation of recognition substances or quenching of phosphors even when numerous phosphors are introduced into the fluorescent label, and also to provide a fluorescently labeled recognition substance which is labeled with the fluoresent label.

As a result of earnest investigation, the inventors of the present invention have found that the fluorescence intensity of a fluorescent label having a structure in which numerous phosphors are bound to a hydrophilic polymer having an anionic group through a polyether derivative can be amplified without denaturing a recognition substance.

In the following, the present invention will be circumstantially explained.

Figure 1:
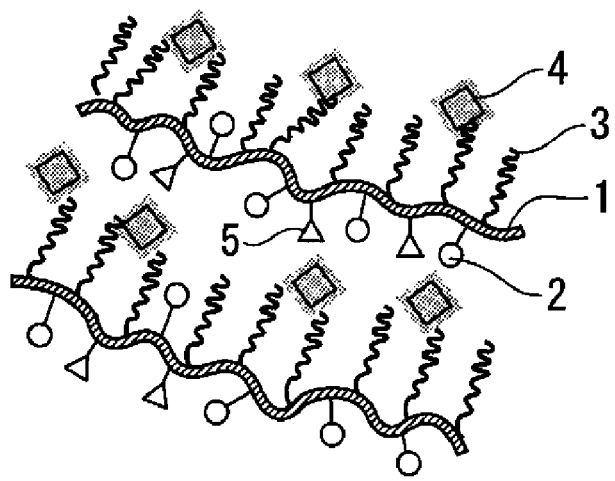
FIG. 1 is a frame format showing a fluorescent label according to the present invention.

FIG. 1 is a frame format showing a structure of a fluorescent label according to the present invention. The numerical symbol 1 indicates a hydrophilic polymer into which an anionic group 5 is introduced. The numerical symbol 2 indicates a hydrophilic substituent other than the anionic group introduced into the hydrophilic polymer 1. The numerical symbol 3 indicates a polyether derivative, and plural polyether derivatives are bound to one hydrophilic polymer 1 via covalent bonds to form a branched chain. At one end of each of a part of the polyether derivatives 3 respectively bound to the hydrophilic polymer 1 at the other end thereof, a phosphor 4 is bound via a covalent bond. A recognition substance is directly bound to a functional group of the hydrophilic polymer 1 via a covalent bond (which is not shown in the drawing).

(Hydrophilic Polymer)

The hydrophilic polymer composing the fluorescent label according to the present invention has a hydrophilic substituent such as an anionic group or the like. Preferable examples of the hydrophilic polymer include polymers in which monomers such as acrylic acid derivatives, vinyl derivatives, or the like are polymerized. Examples of the acrylic acid derivatives include acrylic acid, methacrylic acid, 2-aminoethyl methacrylate, 3-sulfopropyl methacrylate, 2-acrylamido-2-methylpropane sulfonate, 2-ethyl methacrylic acid glucoside, N-acryloxysuccinimide, and the like. Examples of the vinyl derivatives include sodium vinylsulfonate, N-vinyldimethylamine, N-vinyldiethylamine, vinylphosphonic acid dimethyl ester, vinylphosphonic acid diethyl ester, and the like. However, the monomers which can be used are not limited to these compounds. Among these, hydrophilic polymers composed of either an acrylic acid derivative having an amino group or a vinyl derivative and either an acrylic acid derivative having a sulfonic acid or a phosphoric acid group or a vinyl derivative are preferably used. The monomers may be used alone or in combination of at least two kinds thereof.

Examples of the hydrophilic substituent include an anionic group, a hydroxyl group, a thiol group, an amino group, a quaternary ammonium group, and the like.

Moreover, the hydrophilic polymer preferably has a molecular weight of 5 to 500 kDa, and more preferably 5 to 100 kDa.

As a method for preparing the hydrophilic polymer having an anionic group, both a method in which a monomer having an anionic group is polymerized and a method in which a monomer free from an anionic group is polymerized, followed by introducing an anionic group into the obtained polymer can be used.

As the anionic group, a sulfonic acid group, a phosphoric acid group, or salts thereof is preferably used. However, groups other than these, for example, a phosphinic acid group, a sulfinic acid group, a sulfenic acid group, a carboxylic acid group, salts thereof, or the like may also be used.

(Polyether Derivative)

Examples of the polyether derivative composing the fluorescent label according to the present invention include polyethylene glycol derivatives, polypropylene glycol derivatives, and the like.

The polyether derivative is, for example, introduced using a derivative having functional groups such as amino groups at both ends thereof, such as, for example, a polyethylene glycol bis-aminopropyl or a polypropylene glycol bis-aminopropyl, one end functional group thereof being reacted with the hydrophilic polymer and the other end functional group thereof being reacted with the phosphor.

The polyether derivative preferably has a molecular weight of 0.1 to 50 kDa, and more preferably 10 to 30 kDa.

(Phosphor)

Examples of the phosphor composing the fluorescent label according to the present invention include an indacene derivative, a fluorescein derivative, a rhodamine derivative, an indocarbocyanine derivative, a furazan derivative, and the like.

Moreover, a xanthene chromogen, a cyanine chromogen, a coumarin chromogen, a porphyrin chromogen, and fluorochromes such as a composite chromogen or the like may also be used. However, the phosphor used in the present invention is not limited to these. Substances occurring in nature (naturally-occurring substances) are excited with a comparatively short wavelength of approximately 200 nm to 500 nm to emit light. Accordingly, the above-mentioned phosphor which is excited with a wavelength over approximately 500 nm, and more preferably within a spectrum range from approximately 500 nm to 900 nm is used so as to prevent the fluorescence originating from the naturally-occurring substance from being erroneouslly detected in measurement of the fluorescence.

(Fluorescent Label)

The fluorescent label according to the present invention has a structure in which plural polyether derivatives are bound to one hydrophilic polymer via covalent bonds to form a branched chain, and a part of the polyether derivatives is bound at each end thereof to the phosphor via a covalent bond. Since the phosphor is not directly bound to the hydrophilic polymer, each phosphor tends scarcely to aggregate and so the fluorescent label can maintain sufficient hydrophilic properties to prevent the denaturation even when bonded to the recognition substance.

The effect of amplifying the fluorescence intensity can be exhibited even when the number of phosphors introduced into one hydrophilic polymer is one. In order to perform highly sensitive measurement in each case, it is preferable that the number of phosphors introduced into one hydrophilic polymer be 1 to 90, and more preferably 3 to 60. Although 90 or more phosphors can be introduced, the effect of amplifying the fluorescence intensity gradually decreases.

(Fluorescently Labeled Recognition Substance)

The fluorescent label can fluorescently label various recognition substances. Examples of the recognition substances include proteins, peptides, antibodies, antigens, haptens, receptors, nucleic acids, nucleotides, nucleotide derivatives, natural or synthetic medicines, synthetic oligomers, synthetic polymers, hormones, lymphokines, cytokines, toxins, ligands, carbohydrates, sugars, oligosaccharides, polysaccharides, and the like.

The bond between the fluorescent label and the recognition substance is formed by reacting a functional group such as a carboxyl group, an amino group, or the like, of the hydrophilic polymer with a functional group of the recognition substance. For example, when one of the functional groups is a carboxylic acid, a method in which the reaction is performed using a coupling reagent, or a method in which the carboxylic acid is activated to be a carboxylic acid halide, a carboxylic acid anhydride, a carboxylic acid hydrazide, a carboxylic acid azide, activated esters, or the like, followed by reacting it with an amino group of the other functional group may be used. When one of the functional groups is an amino group, a method in which the amino group is thiolated by iminothiolane, followed by binding it to the other amino group using GMBS (N-(4-maleimidobutyryloxy)succinimide) can be used.

In preparation of the fluorescently labeled recognition substance, approximately 1 to 4 recognition substance(s) is(are) preferably introduced into one fluorescent label.

(Immunoassay Reagent Containing Fluorescently Labeled Recognition Substance and Immunoassay Method Using the Reagent)

The fluorescently labeled recognition substance according to the present invention can be used for immunoassay together with various solid phase reagents in which antibodies or the like are bonded and which are generally used for immunoassay. These reagents may be used in well-known sandwich methods or competition methods such as a one-step method, delayed one-step method, two-step method, or the like. The immunoassay can be performed by measuring the fluorescence intensity of the fluorescently labeled recognition substance forming immunocomplexes with antibodies or the like present on the solid phase by immunoreaction. Substances which can be measured are substances which react or interact with the fluorescently labeled recognition substance, and examples thereof include various antigens and antibodies originating from organisms. Examples of samples containing such antigens or antibodies include body fluids such as whole blood, serum, plasma, urine, lymph, and the like, feces extract, and the like.

According to the present invention, it is possible to detect fluorescence having a higher intensity than the total intensity of the fluorescence usually estimated based on the number of phosphors and to make the fluorescent label become supersensitized. Specifically, the fluorescence intensity of the fluorescent label according to the present invention is amplified at least ten times as strong as the total intensity of the fluorescence usually estimated based on the number of phosphors.

The fluorescent label has a significantly improved water solubility, and does not cause denaturation of the fluorescently labeled recognition substance.

Also, according to the present invention, a fluorescently labeled recognition substance having an excellent water solubility and/or detection sensitivity can be obtained.

Also, according to the present invention, the fluorescence immunoassay or the like can be performed with high-sensitivity over a short time. Specifically, the fluorescence-labeling method according to the present invention exhibits approximately the same sensitivity (2S/N) as conventional enzyme-labeling methods, and enables the measurement to be performed over a shorter time than the conventional enzyme-labeling methods, the shortest time periods required for the measurement according to the present invention being approximately one fifth those of the conventional enzyme-labeling methods.

EMBODIMENTS

In the following, the present invention will be explained in more detail with reference to Embodiments. However, it should be apparent that the present invention is not limited to these Embodiments.

Preparation Embodiment 1

(Preparation of Hydrophilic Polymer Composed of 3-Sulfopropyl Methacrylate and 2-Aminoethyl Methacrylate Hydrochloride)

1.97 g of 3-sulfopropyl methacrylate and 0.33 g of 2-aminoethyl methacrylate hydrochloride were put into a 100-ml egg-type flask, into which 25 ml of anhydrous dimethylformamide was then added and dissolved. Next, 163 mg of AIBN was added to the mixture as an initiator and deaerated, followed by replacing with an argon gas. The egg-type flask was immersed in an oil bath heated at 65° C., and reaction was performed for 3 hours. After completing the reaction, 150 ml of dry acetone was added to the egg-type flask, and the produced precipitate was collected by filtration using a glass filter. The obtained precipitate was vacuum-dried while heating at 30 to 40° C. to produce 2.1 g of a hydrophilic polymer composed of 3-sulfopropyl methacrylate and 2-aminoethyl methacrylate hydrochloride.

Embodiment 1

(Preparation of Hydrophilic Polymer)

0.58 g of 2-acrylamido-2-methylpropane sulfonate and 1.13 g of N-acryloxysuccinimide were put into a 200-ml egg-type flask, into which 50 ml of an anhydrous dimethylformamide was then added and dissolved. Next, 163 mg of AIBN was added as an initiator and deaerated, followed by replacing with an argon gas. The egg-type flask was immersed in an oil bath heated at 65° C., and reaction was performed for 3 hours. After completing the reaction, 150 ml of dry ethyl acetate was added to the egg-type flask, and the produced precipitate was collected by filtration using a glass filter. The obtained precipitate was vacuum-dried while heating at 30 to 40° C. to produce 1.3 g of a hydrophilic polymer composed of 2-acrylamido-2-methylpropane sulfonate and N-acryloxysuccinimide.

(Introduction of Polyethylene Glycol Derivative into Hydrophilic Polymer)

50 ml of an aqueous solution containing approximately 4.8 g (corresponding to approximately 200 times as much as the hydrophilic polymer) of polyethylene glycol-bis-3-aminopropane (manufactured by Aldrich Corporation) was prepared, and the pH thereof was adjusted to 7 to 8. Into this solution, a dimethyl sulfoxide solution containing 500 mg of the hydrophilic polymer composed of 2-acrylamido-2-methylpropane sulfonate and N-acryloxysuccinimide (of which average molecular weight was 30,000) was added gradually while stirring. After the reaction was performed at room temperature for 3 hours, an unreacted polyethylene glycol-bis-3-aminopropane was removed by gel-filtration using Superdex 200 (manufactured by Pharmacia Corp.; 35×600 mm, balanced with a buffer of 50 mM CHES-NaOH, pH 10). A fraction containing an objective substance was collected, dialyzed using a dialysis membrane for a whole day and night, and then freeze-dried to produce approximately 720 mg of a hydrophilic polymer composed of 2-acrylamido-2-methylpropane sulfonate and N-acryloxysuccinimide into which polyethylene glycol-bis-3-aminopropane was introduced.

(Preparation of Fluorescent Label)

Next, 5 mg of the hydrophilic polymer including the introduced polyethylene glycol-bis-3-aminopropane was measured and dissolved into 1 ml of 50 mM phosphate buffer. Next, into this solution, 200 μl of a dry dimethyl sulfoxide solution containing 2.7 mg of 4,4-difluoro-5-(2-thienyl)-4-bora-3a, 4a-diaza-s-indacene-3-propionic succinimidyl ester phosphor (manufactured by Molecular Probes, Inc.; hereinafter, abbreviated as BODIPY-560) was added gradually over 30 minutes while stirring. After the addition, stirring was further continued for approximately 2 hours. After completing the stirring, an unreacted BODIPY-560 and dimethyl sulfoxide were removed using PD-10 column (manufactured by Pharmacia Corp.) balanced with purified water. A fraction containing an objective substance was collected and concentrated to approximately 1 ml using an ultrafilter of which cutoff molecular weight was 10,000 (manufactured by Millipore Corporation; Centriprep-10). The concentrated substance was freeze-dried to produce 3.7 mg of the objective substance, that is, a fluorescent label labeled with BODIPY-560.

Embodiment 2

(Preparation of Hydrophilic Polymer)

1.23 g of 3-sulfopropyl methacrylate and 0.98 g of N-acryloxysuccinimide were put into a 200-ml egg-type flask, into which 25 ml of an anhydrous dimethylformamide was then added and dissolved. Next, 163 mg of AIBN was added as an initiator and deaerated, followed by replacing with argon gas. The egg-type flask was immersed in an oil bath heated at 65° C., and reaction was performed for 1 hour. After completing the reaction, 150 ml of dry ethyl acetate was added to the egg-type flask, and the produced precipitate was collected by filtration using a glass filter. The obtained precipitate was vacuum-dried while heating at 30 to 40° C. to produce 1.6 g of a hydrophilic polymer composed of 3-sulfopropyl methacrylate and N-acryloxysuccinimide.

(Introduction of Polyethylene Glycol Derivative into Hydrophilic Polymer)

50 ml of an aqueous solution containing approximately 1.4 g (corresponding to approximately 200 times as much as the hydrophilic polymer) of polyethylene glycol-bis-3-aminopropane (manufactured by Aldrich Corporation) was prepared, and the pH thereof was adjusted to 7 to 8. Into this solution, a dimethyl sulfoxide solution containing 100 mg of the hydrophilic polymer composed of 3-sulfopropyl methacrylate and N-acryloxysuccinimide (of which average molecular weight was 45,000) was added gradually while stirring. After the reaction was performed at room temperature for 3 hours, an unreacted polyethylene glycol-bis-3-aminopropane was removed by gel-filtration using Superdex 200 (manufactured by Pharmacia Corp.; 35×600 mm, balanced with a buffer of 50 mM CHES-NaOH, pH 10). A fraction containing an objective substance was collected, dialyzed using a dialysis membrane for a whole day and night, and then freeze-dried to produce approximately 150 mg of a hydrophilic polymer composed of 3-sulfopropyl methacrylate and N-acryloxysuccinimide into which polyethylene glycol-bis-3-aminopropane was introduced.

(Preparation of Fluorescent Label)

Next, 5 mg of the hydrophilic polymer including the introduced polyethylene glycol-bis-3-aminopropane was measured and dissolved into 1 ml of 50 mM phosphate buffer (pH 7.0). Next, into this solution, 200 μl of a dry dimethyl sulfoxide solution containing 0.32 mg of N-ethyl-N-{5-(N'''-succinimidyloxycarbonyl)penthyl} indocarbocyanine hydrochloride phosphor (manufactured by DOJINDO LABORATORIES; hereinafter, abbreviated as IC3) was added gradually over 30 minutes while stirring. After the addition, stirring was further continued for approximately 2 hours. After completing the stirring, an unreacted IC3 and dimethyl sulfoxide were removed using PD-10 column (manufactured by Pharmacia Corp.) balanced with purified water. A fraction containing an objective substance was collected and concentrated to approximately 1 ml using an ultrafilter of which cutoff molecular weight was 10,000 (manufactured by Millipore Corporation; Centriprep-10). The concentrated substance was freeze-dried to produce 3.8 mg of the objective substance, that is, a fluorescent label labeled with IC3.

Embodiment 3

(Preparation of Fluorescent Label)

5 mg of the hydrophilic polymer composed of 3-sulfopropyl methacrylate and N-acryloxysuccinimide into which polyethylene glycol-bis-3-aminopropane was introduced and which was used in Embodiment 2 was measured and dissolved into 1 ml of 50 mM phosphate buffer. Next, into this solution, 200 μl of a dry dimethyl sulfoxide solution containing 2.7 mg of BODIPY-560 (manufactured by Molecular Probes, Inc.) was added gradually over 30 minutes while stirring. After the addition, stirring was further continued for approximately 2 hours. After completing the stirring, an unreacted BODIPY-560 and dimethyl sulfoxide were removed using PD-10 column (manufactured by Pharmacia Corp.) balanced with purified water. A fraction containing an objective substance was collected and concentrated to approximately 1 ml using an ultrafilter of which cutoff molecular weight was 10,000 (manufactured by Millipore Corporation; Centriprep-10). The concentrated substance was freeze-dried to produce 4.5 mg of the objective substance, that is, a fluorescent label labeled with BODIPY-560.

Embodiment 4

(Preparation of Fluorescently Labeled Recognition Substance)

A buffer contained in 2 ml of α-fetoprotein antibody (2 mg/ml, phosphate buffer solution, pH 7) was replaced with 100 mM carbonate buffer pH 8.5 using PD-0 column (manufactured by Pharmacia Corp.). After replacing the buffer, 117 μl of iminothiolane (1 mg/ml) was added, and reacted for 1 hour at 37° C. while stirring. After completing the reaction, the reactant was concentrated to 2 ml or less using an ultrafilter (manufactured by Sartorius Ltd.; of which cutoff molecular weight was 30,000). After concentrating, the buffer was replaced using PD-10 column (balanced with 50 mM phosphate buffer, pH 6.3) to produce an iminothiolated α-fetoprotein antibody.

Next, 0.9 mg (0.06 μmol) of the fluorescent label prepared in Embodiment 1 was measured and dissolved in a phosphate buffer, pH 7. Into this, 185 μl of a dimethylformamide solution containing 6.2 mg/ml of GMBS (manufactured by DOJINDO LABORATORIES) was added. After the reaction was performed for 1 hour in the dark place, an unreacted GMBS and dimethylformamide were removed using PD-10 column (balanced with 50 mM phosphate buffer, pH 6.3) to obtain a fraction of a fluorescent label bearing GMB.

The iminothiolated α-fetoprotein antibody and the fluorescent label bearing GMB were mixed and reacted in the dark place for a whole day and night. After completing the reaction, an antibody fluorescently labeled with BODIPY-560, that is, a fluorescently labeled recognition substance was obtained using Superdex 200 (manufactured by Pharmacia Corp.).

(Measurement of Fluorescence Intensity of Fluorescent Label)

Test Embodiment 1

(Measurement of Fluorescence Intensity of Fluorescent Label Labeled with BODIPY-560)

Figure 2:
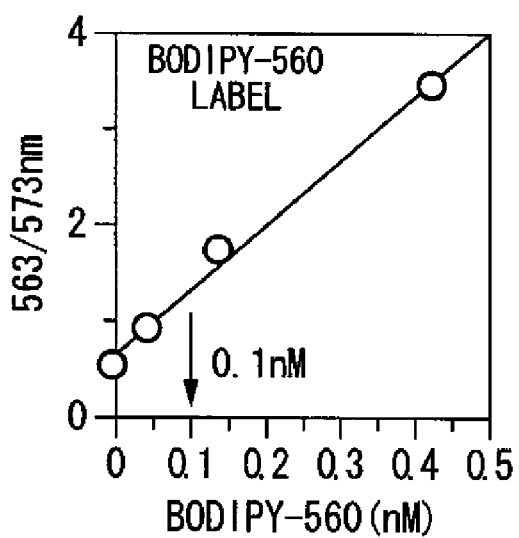
FIG. 2 is a graph indicating the fluorescence intensity of BODIPY-560 contained in a fluorescent label.

1 mg of the fluorescent label prepared in Embodiment 1 was measured and dissolved into 1 ml of 50 mM phosphate buffer (pH 7.0) to prepare 1 mg/ml of a solution. This solution was further diluted 100 times to prepare 10 μg/ml of a solution. This solution was diluted $3^n$ times (n represents an integer from 1 to 7) with the above-mentioned buffer to prepare samples till the dilution ratio reached 1/2187. Each fluorescence intensity of these diluted samples was measured using a fluorometer at an excitation wavelength of 563 nm and a fluorescence emission wavelength of 573 nm. The results are shown in FIG. 2. The vertical axis of FIG. 2 indicates the fluorescence intensity (abbreviated as 563/573 nm) and the horizontal axis indicates the concentration of BODIPY-560.

Test Embodiment 2

(Measurement of Fluorescence Intensity of Fluorescent Label Labeled with IC3)

Figure 3:
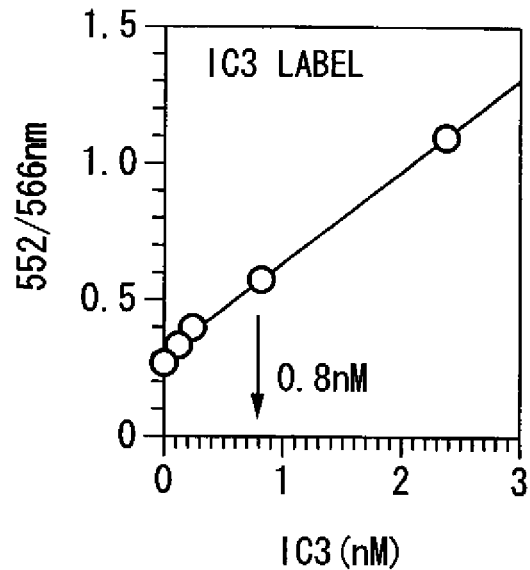
FIG. 3 is a graph indicating the fluorescence intensity of IC3 contained in a fluorescent label.

1 mg of the fluorescent label prepared in Embodiment 2 was measured and dissolved in 1 ml of 50 mM phosphate buffer (pH 7.0) to prepare 1 mg/ml of a solution. This solution was further diluted 100 times to prepare 10 µg/ml of a solution. This solution was diluted $3^n$ times (n represents an integer from 1 to 7) with the above-mentioned buffer to prepare samples till the dilution ratio reached 1/2187. Each fluorescence intensity of these diluted samples was measured using a fluorometer at an excitation wavelength of 552 nm and a fluorescence emission wavelength of 566 nm. The results are shown in FIG. 3. The vertical axis of FIG. 3 indicates the fluorescence intensity (abbreviated as 552/566 nm) and the horizontal axis indicates the concentration of IC3.

Reference Embodiment 1

(Measurement of Fluorescence Intensity of BODIPY-560 alone)

Figure 4:
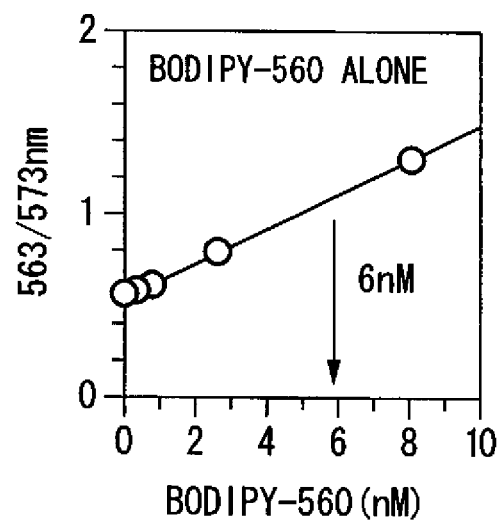
FIG. 4 is a graph indicating the fluorescence intensity of BODIPY-560 alone.

BODIPY-560 was dissolved in a small amount of dimethyl sulfoxide and diluted with 50 mM phosphate buffer (pH 7.0). Moreover, this solution was diluted $4^n$ times (n represents an integer) with the buffer to prepare samples having various final concentrations from 225 nM to 0.3 nM. Each fluorescence intensity of the prepared BODIPY-560 solutions was measured at an excitation wavelength of 563 nm and a fluorescence emission wavelength of 573 nm. The results are shown in FIG. 4. The vertical axis of FIG. 4 indicates the fluorescence intensity (abbreviated as 563/573 nm) and the horizontal axis indicates the concentration of BODIPY-560.

Reference Embodiment 2

(Measurement of Fluorescence Intensity of IC3 alone)

Figure 5:
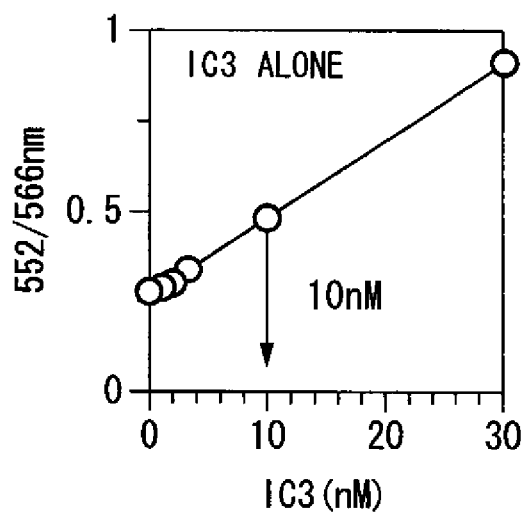
FIG. 5 is a graph indicating the fluorescence intensity of IC3 alone.

A dimethylformamide solution of IC3 was prepared and diluted with 50 mM phosphate buffer (pH 7.0) $3^n$ times (n represents an integer) to prepare samples having various final concentrations from 277 nM to 0.126 nM. Each fluorescence intensity of the prepared IC3 solutions was measured at an excitation wavelength of 552 nm and a fluorescence emission wavelength of 566 nm. The results are shown in FIG. 5. The vertical axis of FIG. 5 indicates the fluorescence intensity (abbreviated as 552/566 nm) and the horizontal axis indicates the concentration of IC3.

When graphs shown in FIGS. 2 and 4 are compared with each other, it is confirmed that the fluorescence intensity of BODIPY-560 in the fluorescent label according to the present invention was amplified to approximately 60 times as strong as that of BODIPY-560 alone, since the fluorescence intensity of BODIPY-560 present alone at the concentration of 6 nM was the same level as that of BODIPY-560 included in the fluorescent label at the concentration of 0.1 nM.

When graphs shown in FIGS. 3 and 5 are compared with each other, it is confirmed that the fluorescence intensity of IC3 in the fluorescent label according to the present invention was amplified to approximately 13 times as strong as that of IC3 alone, since the fluorescence intensity of IC3 present alone at the concentration of 10 nM was at the same level as that of IC3 included in the fluorescent label at the concentration of 0.8 nM.

Embodiment 5

(Immunoassay Using Fluorescently Labeled Recognition Substance)

Immunoassay was performed by ELISA using the fluorescently labeled recognition substance prepared in Embodiment 4.

Figure 6:
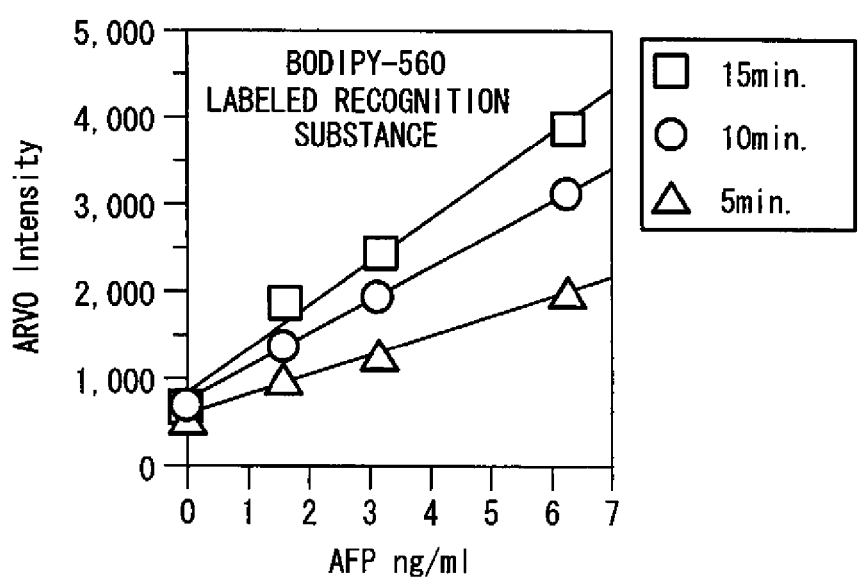
FIG. 6 is a graph indicating results of immunoassay carried out using a fluorescently labeled recognition substance labeled with BODIPY-560.

Duplicate 50-µl aliquots of α-fetoprotein antigen having various concentrations (from 0 to 50 ng/ml) were each added to two wells of three 96-well ELISA plates containing an α-fetoprotein antibody having a recognition site different from that of the fluorescently labeled recognition substance and immobilized in each well thereof in advance. Next, the fluorescently labeled recognition substance prepared in Embodiment 4 was diluted 10 times with phosphate buffer (pH 7.0, 50 mM) and 50 µl of the dilution was then added to each well. After the addition, reaction was performed in an incubator at 37° C. while shaking the plates for 15 minutes, 10 minutes, and 5 minutes, respectively. After completing the reaction, each well was washed four times with Tris-hydrochloride buffer (pH 7) containing 0.01% of Triton X-100. After washing, 100 µl of ethanol was added to each well, and the fluorescence intensity was measured using a fluorescence plate reader (ARVO-sx, manufactured by Wallac, Inc.). The results are shown in FIG. 6. The vertical axis of FIG. 6 indicates the fluorescence intensity (ARVO intensity) and the horizontal axis indicates the concentration of the α-fetoprotein antigen (abbreviated as AFP).

Comparative Embodiment 1

(Preparation of Alkaline Phosphatase-Labeled Antibody and Measurement of α-Fetoprotein by ELISA)

A buffer contained in 278 µl (18 mg/ml) of commercially available alkaline phosphatase (manufactured by Boehringer Mannheim Corporation) was replaced using PD-10 column (manufactured by Pharmacia Corp.) balanced with 0.1M phosphate buffer. The obtained alkaline phosphatase was concentrated to 1 ml using an ultrafilter (Vivaspin manufactured by Sartorius Ltd., of which cutoff molecular weight was 30,000). Into this concentrate, 20 µl of 5 mg/ml GMBS (manufactured by DOJINDO LABORATORIES) dissolved in dimethylformamide was added. After the reaction was performed at room temperature for 1 hour, an unreacted GMBS and dimethylformamide were removed using the above-mentioned PD-10 column to obtain an alkaline phosphatase bearing GMB.

Next, a buffer contained in 2 ml of an α-fetoprotein antibody (2 mg/ml, phosphate buffer solution, pH 7) was replaced with 100 mM of carbonate buffer (pH 8.5) using PD-10 column (manufactured by Pharmacia Corp.). After replacing with 100 mM of carbonate buffer (pH 8.5), 117 µl (1 mg/ml) of iminothiolane was added and reacted at 37° C. for 1 hour while stirring. After completing the reaction, the reactant was concentrated to 2 ml or less using the ultrafilter (manufactured by Sartorius Ltd., of which cutoff molecular weight was 30,000). After concentrating, the buffer was replaced using PD-0 column (equilibrated with 50 mM of phosphate buffer, pH 6.3) to obtain an iminothiolated α-fetoprotein antibody.

The alkaline phosphatase bearing GMB and the iminothiolated α-fetoprotein antibody were mixed and gently stirred at room temperature for 2 hours to react them. After completing the reaction, the reactant was purified using Superdex-200 to obtain an α-fetoprotein antibody labeled with alkaline phosphatase.

Figure 7:
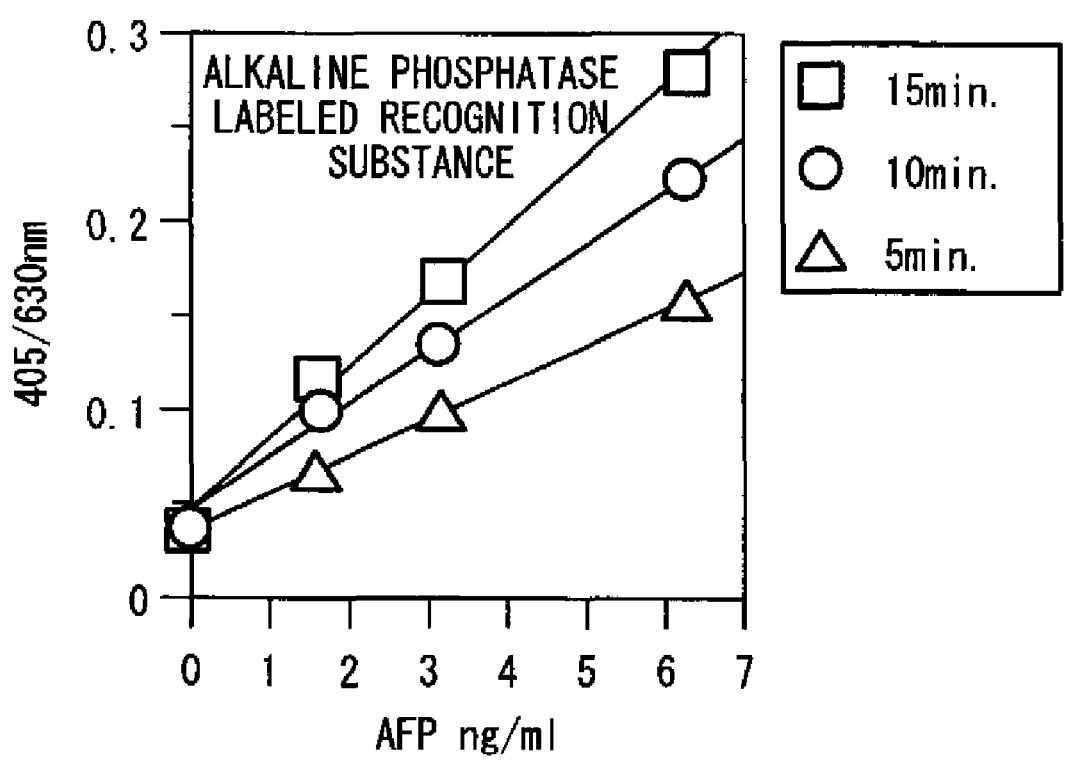
FIG. 7 is a graph indicating results of immunoassay carried out using a label recognition substance labeled with an alkaline phosphatase.

The obtained labeled antibody was used to measure α-fetoprotein. First of all, Duplicate 50-μl aliquots of α-fetoprotein antigen having various concentrations (from 0 to 50 ng/ml) were each added to two wells of three 96-well ELISA plates including an α-fetoprotein antibody having a recognition site different from that of the labeled antibody and immobilized in each well thereof in advance. Next, the above-mentioned labeled antibody was diluted 2000 times with phosphate buffer (pH 7.0, 50 mM) and 50 μl of the dilution was then added to each well. After the addition, reaction was performed in an incubator at 37° C. while shaking the plates for 15 minutes, 10 minutes, or 5 minutes, respectively. After completing the reaction, each well was washed four times with Tris-hydrochloride buffer (pH 7) containing 0.01% of Triton X-100. After washing, 100 μl of 0.1 M diethanolamine-hydrochloride buffer (pH 10.0, containing 1 mM magnesium chloride) substrate liquid containing 10 mM sodium p-nitrophenylphosphate was added to each well, and enzyme reaction was performed for 20 minutes in an incubator at 37° C. while shaking the plates. After completing the reaction, 50 μl of 1M sodium hydroxide was added to stop the enzyme reaction. After sufficiently agitating, the absorbance was measured using a plate reader (MTP-32, manufactured by CORONA ELECTRIC Co., Ltd.) at the wavelength of 405/630 nm. The results are shown in FIG. 7. The vertical axis of FIG. 7 indicates the absorbance intensity (abbreviated as 405/630 nm) and the horizontal axis indicates the concentration of the α-fetoprotein antigen (abbreviated as AFP).

When graphs shown in FIGS. 6 and 7 are compared with each other, it is revealed that the method for labeling with BODIPY-560 exhibited the same detection sensitivity as that in the method for labeling with alkaline phosphatase, when the time period for immobilizing the labeled recognition substance in the ELISA plate was the same for each. According to the method for labeling with alkaline phosphatase, the sensitivity is further improved by elongating the time period for the enzyme reaction. According to the method for labeling with BODIPY-560, the sensitivity is further improved by increasing an energy of light irradiated for fluorescence-detection.

Accordingly, in comparison with the conventional method using an enzyme reaction, the method using the fluorescent label of the present invention exhibits the same detection sensitivity without requiring expensive substrates, and enables measurement over a shorter time because a step of reacting an enzyme with a substrate can be omitted. It is also confirmed that the fluorescent label does not cause denaturation even when numerous phosphors are introduced into antibodies or the like.

As described above, the present invention can provide a fluorescent label which can exhibit high fluorescence intensity using conventional phosphors. Moreover, the present invention is useful in medical fields or other fields, since the use of the fluorescent label does not require specific equipment or the like and enables immunoassay or the like to be performed with high-sensitivity and rapidity at a low cost.

What is claimed is:

1. A hydrophilic polymer having an anionic group;
   a polyether derivative; and
   a phosphor, wherein the phosphor is bound to the hydrophilic polymer via the polyether derivative, the phosphor being an indacene derivative, a fluorescein derivative, a rhodamine derivative, an indocarbocyanine derivative, a furazan derivative, a zanthene chromogen, a cyanine chromogen, a coumarin chromogen or a porphyrin chromogen;
   the hydrophilic polymer is a polymer in which a 3-sulfopropyl methacrylate or a 2-acrylamido-2-methylpropane sulfonate is polymerized, and wherein the anionic group is a sulfonic acid group, a phosphoric acid group, or a salt thereof and wherein the polyether derivative is a polyethylene glycol or polypropylene glycol derivative.

2. A fluorescent label according to claim 1, wherein the hydrophilic polymer a 3-sulfopropyl methacrylate is polymerized.

3. A fluorescent label according to claim 1, wherein the hydrophilic polymer has a molecular weight of 5 to 500 kDa.

4. A fluorescent label according to claim 1, wherein the anionic group contained in the hydrophilic polymer is a sulfonic acid group or salts thereof.

5. A fluorescent label according to claim 1, wherein the polyether derivative is a polyethylene glycol derivative.

6. A fluorescent label according to claim 1, wherein the polyether derivative has a molecular weight of 0.1 to 50 kDa.

7. A fluorescent label according to claim 1, wherein a phosphor number is within a range from 1 to 90.

8. A fluorescent label according to claim 1, wherein the phosphor is an indacene derivative.

9. A fluorescently labelled recognition substance, comprising:
   the fluorescent label of claim 1; and
   a recognition substance; wherein a bond is formed between the fluorescent label and the recognition substance.

10. An immunoassay reagent comprising the fluorescently labeled recognition substance of claim 9.

11. An immunoassay method for detecting an immunocomplex comprising:
    forming immunocomplexes by immunoreaction between the fluorescently labeled recognition substance of claim 9 and either an antibody or antigen that specifically reacts with said fluorescently labeled recognition substance; and
    measuring a fluorescence intensity of the fluorescently labelled recognition substance forming the immunocomplexes.

* * * * *